United States Patent [19]

Krüger et al.

[11] Patent Number: 4,716,152

[45] Date of Patent: Dec. 29, 1987

[54] PHARMACEUTICAL USE OF SUBSTITUTED O-ACYLGLYCOSIDES

[75] Inventors: Bernd-Wieland Krüger, Wuppertal; Oswald Lockhoff, Cologne; Karl G. Metzger, Wuppertal, all of Fed. Rep. of Germany; Hans-Georg Opitz, Emeryville, Calif.; Klaus Schaller; Klaus G. Stünkel, both of Wuppertal, Fed. Rep. of Germany; Hans-Joachim Zeiler, Velbert, Fed. Rep. of Germany

[73] Assignee: Bayer Aktiengesellschaft, Leverkusen, Fed. Rep. of Germany

[21] Appl. No.: 675,808

[22] Filed: Nov. 28, 1984

[30] Foreign Application Priority Data

Dec. 7, 1983 [DE] Fed. Rep. of Germany ....... 3344256

[51] Int. Cl.[4] .............................................. A61K 31/70
[52] U.S. Cl. .................................................... 514/25
[58] Field of Search ........................... 536/4.1; 514/25

[56] References Cited

U.S. PATENT DOCUMENTS 3,597,417  8/1971  Myhre.
3,628,928 12/1971  Gaydasch.
3,772,269 11/1973  Lew ..................................... 536/4.1
4,450,090  5/1984  Kinney ................................ 336/4.1

OTHER PUBLICATIONS

Martin et al., *Chemical Abstacts*, vol. 71 (7), p. 321, 1969, No. 30668g.
Tenside Detergents, 1978, B. Havlinova, pp. 72–74.
Canadian Journal of Chemistry, vol. 46, 1968, A. P. Tulloch et al, pp. 2485–2493.

Liebigs Ann. Chem.-747, 1971-E. Reinefeld et al, pp. 39–44.

*Primary Examiner*—J. R. Brown
*Assistant Examiner*—Elli Peselev
*Attorney, Agent, or Firm*—Sprung Horn Kramer & Woods

[57] ABSTRACT

Compounds of the formula

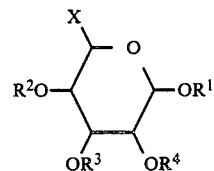

in which
X is hydrogen or the radical $CH_2OR^5$,
$R^2$, $R^3$, $R^4$ and $R^5$ each independently is hydrogen or the radical

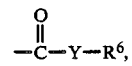

Y is oxygen, sulphur, NH or $CH_2$, and
$R^1$ and $R^6$ each independently is an optionally substituted hydrocarbon radical having up to 50 carbon atoms, with the proviso that at least one of the radicals $R^1$ and/or $R^6$ contains between 9 to 50 carbon atoms, some of which are known, stimulate the immune system's response and antibody production.

13 Claims, No Drawings

PHARMACEUTICAL USE OF SUBSTITUTED O-ACYLGLYCOSIDES

The invention relates to the pharmaceutical use of compounds of the general formula (I)

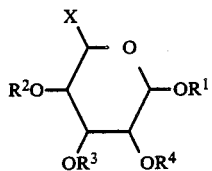

in which
X represents hydrogen or the radical $CH_2OR^5$,
$R^2$, $R^3$, $R^4$ and $R^5$ are identical or different and represent hydrogen or the radical

Y represents oxygen, sulphur, NH or $CH_2$, and
$R^1$ and $R^6$ are identical or different and represent an optionally substituted hydrocarbon radical having up to 50 carbon atoms, with the proviso that at least one of the radicals $R^1$ and/or $R^6$ contains between 9 and 50 carbon atoms.

According to the invention, in the meaning of the radicals $R^1$ and $R^6$, the hydrocarbon radical is to be understood to be a straight-chain or branched alkyl radical, a straight-chain or branched alkenyl radical which is singly or multiply unsaturated, or a saturated or unsaturated alicyclic radical. These meanings can also occur together within the same radical $R^1$ and $R^6$, that is to say, for example, as alkylcycloalkyl, alkenylcycloalkyl, etc.

It is also possible for individual, in general up to 5, preferably 1, 2 or 3, methylene or methine groups in the radicals $R^1$ and $R^6$ to be replaced by O, S and/or N. When the chain is interrupted by N, this nitrogen carries either H or a $C_1-C_{20}$—alkyl radical or a —CO—alkyl radical, this alkyl group having 1-20 C atoms.

Preferably, $R^1$ and $R^6$ represent alkyl or alkenyl radicals having 1 to 21 carbon atoms, preferably having 9 to 21 C atoms, as selected.

Examples of saturated radicals which may be mentioned in this context are: methyl, ethyl, propyl, i-propyl, n-butyl, i-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, docosyl, eicosyl, tetracosyl, triacontyl, ethylpentyl, methyldecyl, i-propyldecyl, methyltridecosyl, pentahexadecyl, 1-dodecylhexadecyl, 2-dodecylhexadecyl, 3-dodecylhexadecyl, 1-hexadecyloctadecyl, 2-hexadecyloctadecyl, 3-hexadecyloctadecyl, 4-hexadecyloctadecyl, 1-octadecyleicosyl and 2-octadecyleicosyl.

Examples of unsaturated radicals are: vinyl, 1-propenyl, 2-propenyl, i-butenyl, 1-butenyl, 2-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-decenyl, 5-decenyl, 9-decenyl, 8-heptadecenyl, 1,3-butadienyl, 1,3-pentadienyl, 1,4-pentadienyl, 2,4-pentadienyl, 8,11-heptadecanedienyl and 8,11,14-heptadecanetrienyl. In general, the longer-chain unsaturated radicals are preferred, in particular the singly or doubly unsaturated alkenyls having 9-21 C atoms. The unsaturated hydrocarbon radicals can also be in the form of pure cis or trans isomers or as mixtures of isomers.

Examples of cycloalkyl which may be mentioned are: cyclopentyl, cyclohexyl and cyclododecyl.

Examples of alkylcycloalkyl radicals which may be mentioned are: methylcyclopentyl, ethylcyclopentyl, n-propylcyclopentyl, i-propylcyclopentyl, n-butylcyclopentyl, octylcyclopentyl, methylcyclohexyl, ethylcyclohexyl, propylcyclohexyl, butylcyclohexyl, hexylcyclohexyl, decylcyclohexyl, cyclopentylmethyl, cyclopentylethyl, cyclopentylpropyl, cyclopentylbutyl, cyclopentylpentyl, cyclopentylhexyl, cyclopentyloctyl, cyclopentyldecyl, cyclohexylmethyl, cyclohexylethyl, cyclohexylpropyl, cyclohexylbutyl, cyclohexylhexyl, cyclohexyldecyl, cyclopentylcyclohexylethyl, cyclohexylcyclopentylethyl and cyclohexylcyclohexylethyl.

The radicals $R^1$ and $R^6$ can be substituted, in general 1-5 times, preferably 1-3 times. Suitable substituents are preferably the following: halogen, preferably F, Cl or Br, amino, $C_1-C_6$-alkylamino, di-$C_1-C_6$-alkylamino, oxo, OH, $C_1-C_6$-alkoxy, SH, $C_1-C_6$-alkylthio, $C_1-C_6$-alkyl-COO and $C_1-C_6$-alkyl-CO-NH.

Examples of cases in which the hydrocarbon radicals $R^1$ and $R^6$ in formula I are interrupted or substituted by O, S and N or corresponding groups of atoms are methoxyethyl, ethoxyethyl, n-propoxyethyl, n-butoxyethyl, i-propoxyethyl, i-butoxyethyl, sec.-butoxyethyl, methoxyethoxyethyl, ethoxyethoxyethyl, propoxyethoxyethyl, i-propoxyethoxyethyl, n-butoxyethoxyethyl, i-butoxyethoxyethyl, sec.-butoxyethoxyethyl, methoxyethoxyethoxyethyl, ethoxyethoxyethoxyethyl, n-butoxyethoxyethoxyethyl, i-butoxyethoxyethoxyethyl, sec.-butoxyethoxyethoxyethyl, when Y represents oxygen, sulphur, $CH_2$ or NH, methoxyethoxy, ethoxyethoxy, n-propoxyethoxy, i-propoxyethoxy, n-butoxyethoxy, i-butoxyethoxy, sec.-butoxyethoxy, methoxyethoxyethoxy, ethoxyethoxyethoxy, n-propoxyethoxyethoxy, i-propoxyethoxyethoxy, n-butoxyethoxyethoxy, i-butoxyethoxyethoxy, sec.-butoxyethoxyethoxy, when Y represents $CH_2$, hydroxyheptadecenyl, oxobutyl, the aminodecyl, N-methylaminodecyl, fluoromethyl, β-hydroxytridecyl or mercaptoethyl radical.

The compounds of the formula I contain several chiral C atoms and are in the form of optically pure diastereomers or mixtures of diastereomers.

The compounds of the formula I to be used according to the invention are thus 0-(cyclo)alkylglycosides which are provided on one or more hydroxyl groups of the saccharide moiety with an acyl, alkoxycarbonyl, alkylthiocarbonyl or carbamoyl radical.

Compounds which are provided on the hydroxyl group in position 6 as saccharide moieties with an acyl, alkoxycarbonyl, alkylthiocarbonyl or a carbamoyl radical are particularly preferred.

Some of the compounds of the formula (I) are known (compare Belgian Patent No. 873,132; U.S. Pat. No. 3,597,417; U.S. Pat. No. 3,628,928; B. Harlinova, et al., Tenside Deterg. 1978, 72; A. T. Tulloch et al., Canad. J. Chem., 46, 2485 (1968); E. Reinefeld et al., Justus Liebigs Ann. Chem. 747, 39 (1971).

The compounds of the formula (I) can be prepared by reacting 0-glycosides of the formula (II) which are known per se or can be prepared by known processes (compare Methods in Carbohydrate Chemistry Academic Press, New York and London, 1972)

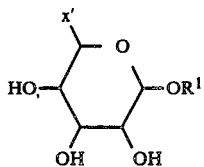
(II)

in which
x' represents H or CH$_2$OH and
R$^1$ has the abovementioned meaning, either in the free, that is to say unprotected form, or in the form of protected, optionally activated, derivatives, with a carbonyl derivative of the formula

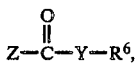

in which
R$^6$ and Y have the abovementioned meaning, and
Z represents halogen, preferably chlorine
or a leaving group which is customary for acylation reactions, preferably an activating ester radical, or a group O—OC—R$^6$, or with an isocyanate of the formula R$^6$—NCO, the reaction being carried out in an organic solvent or aqueous organic solvent at temperatures between −80° and 160° C., preferably between −20° and 60° C., where appropriate in the presence of a base, and, when reaction is complete, working up the reaction product, where appropriate after splitting off any protective groups which may be present, in a customary manner.

Carbonyl derivatives

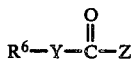

which are known per se and which are to be preferred are anhydrides, activated esters and acid halides, preferably chlorides.

These compounds are preferably reacted with the O-glycosides in the presence of a diluent in which the reactants are completely or only partially dissolved.

Organic or inorganic solvents are suitable, preferably those which, under the reaction conditions, suppress side reactions as far as possible, or prevent them.

It is possible to carry out the reaction either in organic solvents, such as ethers, for example tetrahydrofuran and dioxane, or alcohols, for example ethanol and propanol, or ketones, for example acetone or methyl ethyl ketone, or in dimethylformamide, ethyl acetate or pyridine, or in mixtures of these solvents with one another and/or with water. In general, the use of anhydrous solvents is to be preferred.

The acid derivatives

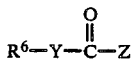

or isocyanates R$^6$—NCO are used in 1–10 equivalents relative to O-glycoside.

It is possible to carry out the reactions, preferably when using acid halides and anhydrides, in the presence of basic auxiliaries. It is possible to use all basic compounds customary in organic synthesis, for example tertiary aliphatic or aromatic amines, or alkali metal and alkaline earth metal hydroxides or carbonates, such as sodium hydroxide solution, sodium carbonate or calcium carbonate.

The diagram below is intended to illustrate by means of an example one of the preferred embodiments of the preparation according to the invention of compounds of the formula I:

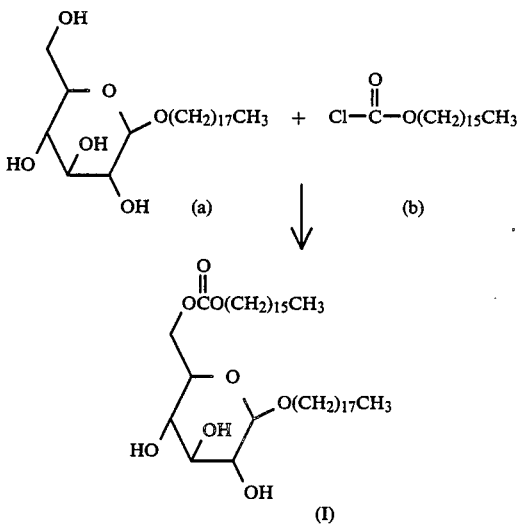

Stearyl-β-D-glucopyranoside (a) is reacted with hexadecyl chloroformate (b) to give stearyl-6-0-hexadecyloxycarbonyl-β-D-glucopyranoside (I).

The present class of compounds exhibits a resistance-increasing effect. It has been found that the class of compounds increases, in an antigen-specific manner, the synthesis of antibodies by the immune system and, moreover, potentiates the non-specific resistance inherent to the host. These results were obtained by using the following designs of experiments.

INCREASE IN THE PRIMARY HUMORAL IMMUNITY IN VIVO TOWARD THE SOLUBLE ANTIGEN OVALBUMIN

NMRI mice were immunized subcutaneously (s.c.) with a suboptimal dose of antigen (1 μg/animal, day 0). With suboptimal antigen stimulation, only a small number of lymphocytes in the animals was stimulated to synthesize antibodies. Additional treatment of the animals with compounds of the examples mentioned of the present invention is able, with a single administration of 10–30 mg/kg, to increase significantly the antibody titre in the serum of the animals. The antibody titre was determined by indirect haemagglutination on day 10. The effect of the treatment is expressed by the geometric mean of log$_2$ titre.

In contrast to other immunostimulants, for example bacterial, such as LPS from Gram-negative bacteria, the immunostimulant effect of the compounds mentioned is antigen-dependent, that is to say the substances surprisingly only induce the synthesis of antibodies when combined with an antigenic stimulus (in this instance ovalbumin or SE). In contrast to the conventional immunostimulants mentioned, they have no mitogenic properties.

TOLERABILITY AND POSSIBLE USES

Although compounds of the type described display their potentiating effect on the mouse after, for example, a single dose of only 10 mg/kg i.p. or orally, no toxic effects are observed even on administration of 100 mg/kg. Thus, the substances mentioned are well tolerated.

The compounds to be used according to the invention have the ability of, on the one hand, increasing the immunity of an antigen when mixed with it, and, on the other hand, of increasing the immunological reactivity of the treated organism on systemic administration. This entails the substances mentioned being able to activate the lymphocytes responsible for the formation of antibodies.

Thus, the compounds of the formula I can be used. as adjuvants mixed with vaccines to improve the success of vaccination and to increase the protection against infection, by bacterial, viral or parasitic pathogens, which is conferred by immunity.

Furthermore, the compounds of the formula I are suitable, when mixed with a wide variety of antigens, as adjuvants in the experimental and industrial preparation of antisera for therapy and diagnosis.

Moreover, the compounds of the formula I can be used, even without simultaneous administration of antigen, to promote defence reactions already taking place at a subthreshold level in humans and animals. Accordingly, the compounds are particularly suitable for stimulation of the body's own resistance, for example where there are chronic and acute infections or where there are selective (antigen-specific) immunological deficits, as well as where there are congenital as well as acquired general (that is to say not antigen-specific) states of immunological deficit, as occur in the elderly, during the course of severe primary diseases and, in particular, after therapy with ionizing radiation or with substances having immunosuppressive activity. The substances mentioned can thus preferably be administered in combination with anti-infectious antibiotics, chemotherapeutic agents or other courses of treatment in order to counteract immunological damage. Finally, the substances described are also suitable for general prophylaxis of infectious diseases in humans and animals.

The compounds of the formula I increase the survival rate in the animal model of sytemic candidosis of the mouse and of acute bacterial infection.

DESCRIPTION OF THE EXPERIMENT

Type SPF-CFWI mice were infected intravenously with $2-6 \times 10^5$ cells of Candida albicans, growing logarithmically, suspended in physiological saline.

The first symptoms of the disease become recognizable in untreated control animals starting on the 3rd day after infection. By the 5th day, the first animals have died of acute renal failure, and by the 14th day after infection, as a rule, more than 80% of the untreated animals have died. In this test, the compounds of the formula I act to retard the disease. A significant action retarding the disease was achieved when the substance (Example 1) was administered intraperitoneally (i.p.) in each case 24 hours before infection, at concentrations of 1-50 mg/kg body weight.

A statistically significant prolongation of the survival time of treated animals compared with untreated controls was observed. About 50% of the untreated animals survived an observation period of 14 days, compared with about 20% of untreated control animals.

The compounds of the formula I can be used alone as a prophylactic agent to combat existent infections, or can be used in combination with antibiotic therapy to increase the therapeutic effect of antibiotics and chemotherapeutic agents (for example penicillins, cephalosporins, aminoglycosides etc.) in infected humans and animals.

It has been found that infections of the mouse with pathogenic organisms which lead to death within 24-48 hours can be treated by a prophylactic treatment, preferably intraperitoneally, with 1-80 mg/kg of the compounds of the formula I. This applies to a whole series of Gram-positive (for example Staphylococci) and Gramnegative (for example *E. coli*, Klebsiella, Proteus and Pseudomonas) pathogens. This list is to be understood to be of examples and by no means as restrictive. Thus, for example, 40-100% of mice which have been infected with the pathogenic strain Klebsiella 63 survive this infection after treatment (for example 18 hours before infection) with 10-40 mg/kg of the compound (Example 1), while only 0-30% of the untreated control animals survived.

In another experimental model, it was possible to show that the therapeutic efficacy of antibiotics can be increased by the compounds of the formula I. Thus, mice were infected with the strain Pseudomonas W. This infection led to the death of most of the control animals within 24 hours. Another group was treated with 4 mg/kg sisomicin 30 hours after infection. It was possible to show that it was possible crucially to improve the therapeutic efficacy of sisomicin in the experimental group which had been treated with the compounds of the formula I 18 hours before infection.

The invention also relates to pharmaceutical formulations which contain compounds of the formula I. They are preferably tablets or gelatine capsules which contain the active compounds together with diluents, for example lactose, mannitol, sorbitol, cellulose and/or lubricants, for example diatomaceous earths, talc, stearic acid or salts thereof, such as magnesium or calcium stearate, and/ or polyethylene glycol. Tablets likewise contain binders, for example magnesium silicate, starches, such as corn, wheat, rice or arrowroot starch, gelatine, tragacanth, methylcellulose, sodium carboxymethylcellulose and/or polyvinylpyrrolidone, and, if desired, disintegrants, for example starches, agar, alginic acid or a salt thereof, such as sodium alginate and/or effervescent mixtures or adsorption agents, colorants, flavorings and sweeteners. Injectable products are preferably isotonic aqueous solutions or suspensions. Suppositories, ointments or creams are primarily fatty emulsions or suspensions. The pharmaceutical products can be sterilized and/or contain auxiliaries, for example preservatives, stabilizers, wetting and/or emulsifying agents, solubilizers, salts to regulate the osmotic pressure and/or buffers. The pharmaceutical products according to the invention which, if desired, can contain other pharmacologically valuable substances, are prepared in a manner known per se, for example using conventional mixing, granulating or coating processes, and they contain from about 0.1% to about 75%, in particular from about 1% to 50%, of the active compounds mentioned.

Products for oral administration can also be provided with a coating resistant to gastric juice.

The compounds of the formula I can be used as resistance-increasing and immunopotentiating agents for the treatment of chronic and acute infections (for example bacterial, viral and parasitic) and malignant tumors. They can likewise be used as adjuvants in vaccination, in the stimulation of phagocytosis, and in dysregulation of the defense immune system.

PREPARATION EXAMPLES

(1) Methyl-6-0-(1-undecyl)-nonadecyloxycarbonyl-D-glucopyranoside

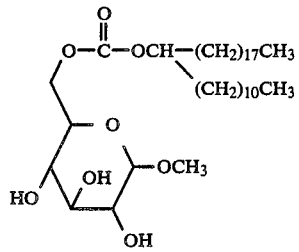

8.9 g (0.046 mol) of 1-0-methyl-D-glucopyranoside are suspended in 5.1 g of triethylamine and 150 ml of tetrahydrofuran and, at an internal temperature of 0° C., 23.1 g (0.046 mol) of (1-undecyl)-nonadecyl chloroformate are added. The mixture is warmed at 40° C. for 3 days, and the solid is filtered off and the solvent is removed by distillation under waterpump vacuum. The residue is chromatographed on silica gel (400 g of Merck silica gel 60; particle size 0.040–0.063 mm; mobile phase: toluene: isopropanol=10:1), and 1.2 g of methyl-6-0-(1-undecyl)nonadecyloxycarbonyl-D-glucopyranoside having a Rf value of 0.44 (toluene:isopropanol=6 : 1; Merck TLC aluminium foil; silica gel 60 $F_{254}$; layer thickness 0.2 mm) is obtained.

(2) Methyl-6-0-palmitoyl-α-D-glucopyranoside

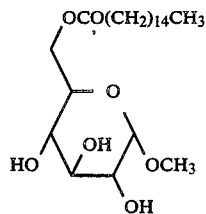

411 mg (1 mmol) of methyl-2,3,4-0-tris-trimethylsilyl-α-D-glucopyranoside, 256 mg (T mmol) of palmitic acid and 206 mg (1 mmol) of dicyclohexylcarbodiimide in 10 ml of methylene chloride are stirred at 20° C. for 4 hours. After filtering off the urea, it is thoroughly washed with methylene chloride, and the solvent is removed by distillation under waterpump vacuum. Methyl-2,3,4-0-tris-trimethylsilyl-6-0-palmitoyl-α-D-glucopyranoside with an Rf value of 0.45 (ether: petroleum ether=1:1, Merck plates Cat. No. 5719) is obtained in quantitative yield.

700 mg (1.08 mmol) of this product are dissolved in 10 ml of hot $CH_3OH$, and water (10 ml) is added. The mixture is heated under reflux for 4 hours, and then volatile products are removed under high vacuum. Methyl-6-0-palmitoyl-α-D-glucopyranoside with an Rf value of 0.19 ($CH_3OH:H_2O=15:1$) is obtained in quantitative yield.

The following are obtained analogously:

$$\text{structure with } OC-Y-R^6, OR^1, OH^y$$

| | $R^1$ | $OH^y$ | $R^6$ | Rf value* |
|---|---|---|---|---|
| 3. | $CH_3$ | O | $-CH(\text{(CH}_2)_8CH_3)(\text{(CH}_2)_8CH_3)$ | 0.26 |
| 4. | $CH_3$ | O | $-CH(\text{(CH}_2)_{16}CH_3)(\text{(CH}_2)_{17}CH_3)$ | |
| 5. | $CH_3$ | O | $-CH(\text{(CH}_2)_{14}CH_3)(\text{(CH}_2)_{17}CH_3)$ | |
| 6. | $CH_3$ | O | $-CH\underset{\hspace{1em}}{\phantom{x}}(CH_2)_{11}$ (cyclic) | 0.37 |
| 7. | $CH_3(CH_2)_{11}$ | O | $-(CH_2)_{11}CH_3$ | |
| 8. | $CH_3(CH_2)_{11}$ | $CH_2$ | $-(CH_2)_{11}CH_3$ | |
| 9. | $CH_3(CH_2)_{17}$ | $CH_2$ | $-(CH_2)_{10}CH_3$ | |
| 10. | $CH_3(CH_2)_{17}$ | $CH_2$ | $-(CH_2)_{15}CH_3$ | |
| 11. | $CH_3(CH_2)_{17}$ | NH | $-(CH_2)_{17}CH_3$ | |

-continued

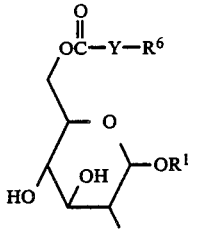

| | R¹ | OH$^y$ | R⁶ | Rf value* |
|---|---|---|---|---|
| 12. | CH₃(CH₂)₁₇ | S | —(CH₂)₁₁CH₃ | |

*(Toluene: i-PrOH = 6:1) Merck TLC plates, Cat. No. 5714

It will be understood that the specification and examples are illustrative but not limitative of the present invention and that other embodiments within the spirit and scope of the invention will suggest themselves to those skilled in the art.

What is claimed:

1. A method of activating the immune system of a patient which comprises administering to a patient an amount effective therefor of a compound of the formula

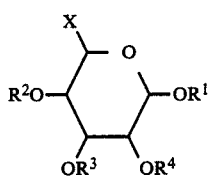

in which

X is hydrogen or the radical CH$_2$OR$^5$,

R$^2$, R$^3$, R$^4$ and R$^5$ each independently is hydrogen or the radical

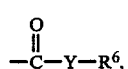

Y is oxygen, sulphur, NH or CH$_2$, and

R$^1$ and R$^6$ each independently is a hydrocarbon radical having up to 50 carbon atoms, or a hydrocarbon radical having up to 50 carbon atoms wherein up to 5 methylene or methine groups are replaced by O, S, NH, N—C$_{1-20}$-alkyl or N—CO—C$_{1-20}$-alkyl, with the proviso that at least one of the radicals R$^1$ and R$^6$ contains between 9 to 50 carbon atoms.

2. The method according to claim 1, in which R$^1$ and R$^6$ each independently is an alkyl or alkenyl radical having 1-21 carbon atoms, or an alkyl or alkenyl radical having 1-21 carbon atoms wherein up to 5 methylene or methine groups are replaced by O, S, NH, N—C$_{1-20}$-alkyl or N—CO—C$_{1-20}$-alkyl.

3. The method according to claim 1, in which X is CH$_2$OR$^5$, and R$^5$ is

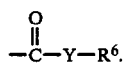

4. The method according to claim 1, wherein such compound is methyl-6-0-(1-undecyl)-nonadecyloxycarbonyl)-D-glucopyranoside of the formula

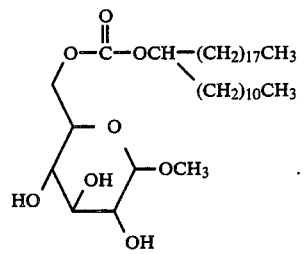

5. The method according to claim 1, wherein said compound is methyl-6-0-palmitoyl-α-D-glucopyranoside of the formula

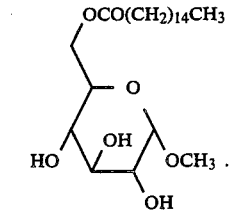

6. The method according to claim 1, wherein such compound is methyl-6-0-(1-nonyl)-decyloxycarbonyl)-D-glucopyranoside of the formula

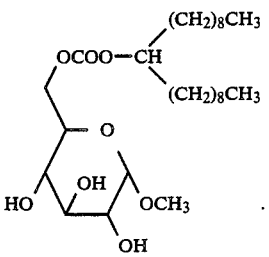

7. The method according to claim 1, wherein such compound is methyl-6-0-(1-Heptadecyl)-nonadecyloxycarbonyl)-D-glucopyranoside of the formula 8. The method according to claim 1, wherein such compound is methyl-6-0-(1-Pentadecyl)-nonadecyl-oxycarbonyl)-D-glucopyranoside of the formula

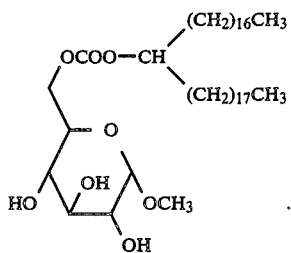

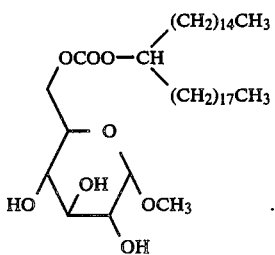

9. The method according to claim 1, wherein such compound is methyl-6-0(cyclododecyloxycarbonyl)-D-glucopyranoside of the formula

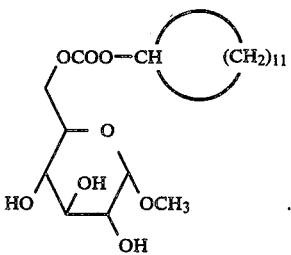

10. A unit dose of a composition comprising a pharmaceutically acceptable diluent and an immune system-activating amount of a compound of the formula

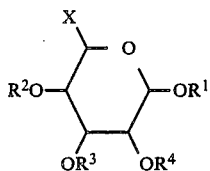

in which
X is hydrogen or the radical $CH_2OR^5$,
$R^2$, $R^3$, $R^4$ and $R^5$ each independently is hydrogen or the radical

Y is oxygen, sulphur, NH or $CH_2$, and
$R^1$ and $R^6$ each independently is a hydrocarbon radical having up to 50 carbon atoms, or a hydrocarbon radical having up to 50 carbon atoms wherein up to 5 methylene or methine groups are replaced by O, S, NH, N—$C_{1-20}$-alkyl or N—CO—$C_{1-20}$-alkyl, with the proviso that at least one of the radicals $R^1$ and $R^6$ contains between 9 to 50 carbon atoms.

11. A unit dose according to claim 10 in the form of a tablet, capsule or injectable solution.

12. A unit dose according to claim 10, wherein such compound is
methyl-6-0-(1-undecyl)-nonadecyloxycarbonyl)-D-glucopyranoside,
methyl-6-0-palmitoyl-α-D-glucopyranoside,
methyl-6-0-(1-nonyl)-decyloxycarbonyl)-D-glucopyranoside,
methyl-6-0-(1-Heptadecyl)-nonadecyloxycarbonyl)-D-glucopyranoside,
methyl-6-0-(1-Pentadecyl)-nonadecyloxycarbonyl)-D-glucopyranoside, and
methyl-6-0-(cyclododecyloxycarbonyl)-D-glucopyranoside.

13. A unit dose according to claim 10 in the form of a tablet or capsule.

* * * * *